United States Patent [19]

Walz

[11] Patent Number: 5,401,651

[45] Date of Patent: Mar. 28, 1995

[54] DNA ENCODING ENA-78, A NEUTROPHIL ACTIVATING FACTOR

[76] Inventor: Alfred Walz, Feldrainstrasse 7, 3098 Koeniz, Switzerland

[21] Appl. No.: 778,413

[22] Filed: Oct. 16, 1991

[51] Int. Cl.$^6$ .................. C12N 15/19; C12N 15/66; C12N 5/10

[52] U.S. Cl. .................. 435/240.2; 536/23.5; 435/320.1; 435/252.3; 435/69.1; 435/69.5; 530/350

[58] Field of Search .............. 536/27, 23.5; 435/69.1, 435/69.5, 240.2, 320.1, 252.3

[56] References Cited

PUBLICATIONS

A Novel Neutrophil-Activating Factor Produced by Human Mononuclear Phagocytes, Walz et al., J. Exp. Med., vol. 167 May 1988, 1547–1559.

Purification and Partial Biochemical Characterization of a Human Monocyte-Derived, Neutrophil-Activating Peptide That Lacks Interleukin Activity, Schröder et al., J. of Immun. vol. 139 Nov. 1987, 3474–3483.

Purification of a Human Monocyte-derived neutrophil chemotactic factor that has peptide sequence similarity to other host defense cytokines, Yoshimura, et al., Proc. Natl. Acad. Sci. USA, vol. 84, Dec. 1987, 9233–9237.

Neutrophil-Activating Peptide-1/Interleukin 8, a Novel Cytokine That Activates Neutrophils, Baggiolini et al., J. Clin. Invest., vol. 84, Oct, 1989, 1045–1049.

A Novel Cleavage Product of B-Thromboglobulin Formed in Cultures of Stimulated Mononuclear Cells Activates Human Neutrophils, Walz et al., Biochem. & Biophys. Res. Comm., vol. 159, Mar. 1989, 969–975.

Generation of the Neutrophil-Activating Peptide NAP-2 from Platelet Basic Protein or Connective Tissue Activating Peptide III through Monocyte Proteases, Walz et al., J. Exp. Med., vol. 171, Feb. 1990, 449–454.

Amino Acid Sequence of Human Platelet Factor 4, Deuet et al., Proc. Natl. Acad. Sci. USA, vol. 74 Jun. 1977, 2256–2258.

Biochemical Characterizaton of a Interferon-Inducible Cytokine (IP-10), Uster et al., J. Exp. Med., vol. 166, Oct. 1987, 1084–1097.

Macrophages Cultured in Vitro Release Leukotriene B4 and Neutrophil Attractant/Activation Protein (Interleukin 8) Sequentially in Response to Stimulation with Lipopolysaccharide and Zymosan, Rankin et al., J. Clin. Inv., vol. 86, No. 1990, 1556–1564.

Molecular Characterization and Chromosomal Mapping of Melanoma Growth Stimulatory Activity, a Growth Factor Structurally Related to B-Thromboglobulin, Richmond et al., EMBO J. vol. 7, 1988, 2025–2033.

Neutrophil-Activating Properties of the Melanoma Growth Stimulatory Activity, Moser et al., J. Exp. Med., vol. 171, May 1990, 1797–1802.

NH-2-Terminal Amino Acid Sequence Identity with Melanoma Growth Stimulator, Activity, Schroöder et al., J. Exp. Med., vol. 171, Apr. 1990, 1091–1100.

Endothelial Cell Gene Expression of a Neutrophil Chemotactic Factor by TNF-$\beta$, LPS, and IL-1B, Strieter et al., Science, vol. 243, 1989, 1467–1469.

(List continued on next page.)

*Primary Examiner*—Garnette D. Draper
*Assistant Examiner*—David L. Fitzgerald
*Attorney, Agent, or Firm*—Robert R. Cook

[57] ABSTRACT

The invention relates to a novel factor comprising a polypeptide denominated ENA-78, said factor being derived from epithelial cells and having the ability to activate neutrophils, as well as DNA coding for such factors, methods of treating neutrophil deficiencies, methods of identifying inhibitors of ENA-78 using a novel assay, the inhibitors identified by such an assay, and methods for treating acute and chronic lung disorders using such inhibitors.

6 Claims, 10 Drawing Sheets

```
ENA-78    A G P A A A V L R E L R C V C L Q T T Q - G V H P K M I S N L Q
IL-8      S A K E L R C Q C I K T Y S K P F H P K F I K E L R
NAP-2     A E L R C M C I K T T S - G I H P K N I Q S L E
GROα      A S V A T E L R C Q C L Q T L Q - G I H P K N I Q S V N
GROβ      . P L . . . . . . . . . . . . . . - . . . . L . . . . . . . K
GROγ      . . . V . . . . . . . . . . . . . - . . . . L . . . . . . . .
PF-4      E A E E D G D L Q C L C V K T T S - Q V R P R H I T S L E
γIP-10    V P L S R T V R C T C I S I N Q - P V N P R S L E K L E

ENA-78    V F A I G P Q C S K V E V V A S L K N - G K E I C L D P E A P F L K K V I Q K I L D G G N K E N
IL-8      V I E S G P H C A N T E I I V K L S D - G R E L C L D P K E N H V Q R V V E K F L K R A E N S
NAP-2     V I G K G T H C N Q V E V I A T L K D - G R K I C L D P D A P R I K K I V Q K K L A G D E S A D
GROα      V K S P G P H C A Q T E V I A T L K N - G R K A C L N P A S P I V K K I I E K M L N S D K S N
GROβ      . . . . . . . . . . . . . . . . . . . - . Q . . . . . . . . . M . . . . . . . . . . K N G . . .
GROγ      . R . . . . . . . . . . . . . . . . . - . K . . . . . . . . . M . Q . . . . . I . . K G S T .
PF-4      V I K A G P H C P T A Q L I A T L K N - G R K I C L D L Q A P L Y K K I I K K L L E S
γIP-10    I I P A S Q F C P R V E I I A T M K K K G E K R C L N P E S K A I K N L L K A V S K E M S K R S P
```

PUBLICATIONS

Human Alveolar Macrophage Gene Expression of Interleukin-8 by Tumor Necrosis Factor-α, Lipopolysaccharide, and Interluekin-1B, Strieter et al., Am. J. Respir. Cell Mol. Biol., vol. 2, 1990, 321–326.

A Model for Cytokine Networks in the Lung Standford et al., J. Clin. Invest., vol. 86, Dec. 1990, 1945–1953.

Inflammatory cytokines induce synthesis and secretion of gro protein and a neutrophil chemotactic factor but net B2-microglobulin in human synovial cells and fibroblasts, Golds et al., Biochem J., vol. 259, 1989, 585–588.

Schroeder et al, *Biochem Biophys Res Comm.* 172(2) 1990, pp. 898–904.

Schroder et al, *J. Exp Med* 171, 1990, pp. 1091–1100.

Mukaida et al, *J. Biol Chem* 265 19 pp. 211–228.

Lu et al, *Mol. Cell Biol* 10, 1990, pp. 1982–1988.

Beaubien et al, *Biochem J* 1990, 271, pp. 797–801.

Jose et al. *Biochem J* 1991, 278, pp. 493–497.

Schroder et al, *J Immunol* 144, 1990, pp. 2223–2232.

Walz et al, *J. Exp. Med.* 174(6), 1991, pp. 1355–1362.

De Lorme et al, Cotton Dust 13th 82–84, 1989.

Goodman et al. Biochemistry 1992, v 31, pp. 10483–10490.

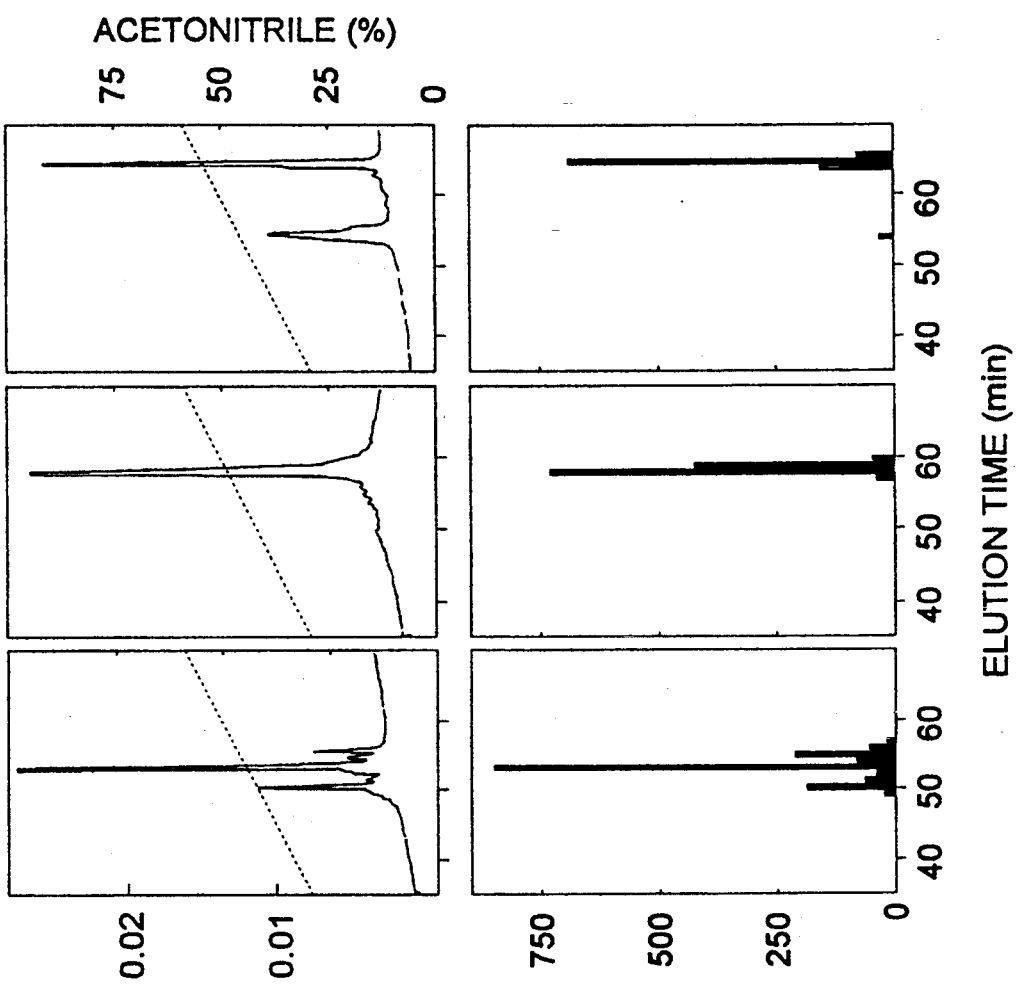
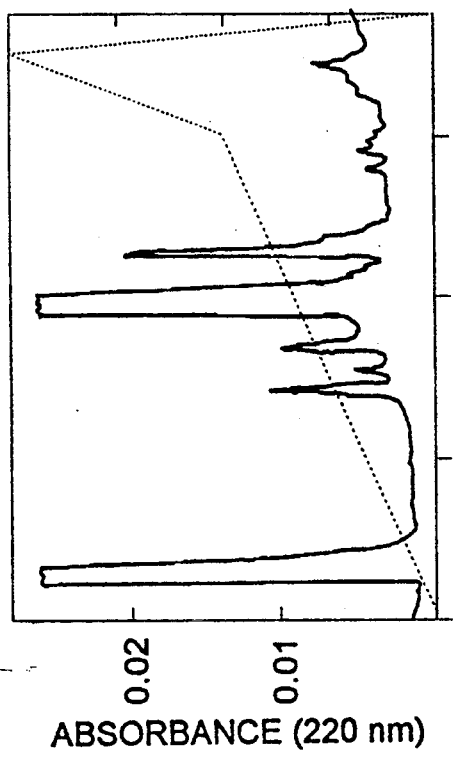
FIG. 2A  FIG. 2B  FIG. 2C  FIG. 2D

FIG. 4

ENA-78, NH2-terminus: AGPAAAVLRELRCVCLQTTQGVHPKMISNLQVFA

ENA-78, COOH-terminus: DPEAPFLKKVIQKILDGGNKEN

GROα: ASVATELRCQCLQ

GROγ: ASVVTELRCQCLQ

IL-8 (77): AVLPRSAKELRCQCIKTYSK

FIG. 5A

```
5'
tcgaattcGTIYTISGIGAACTISGITGYGTTG    3'
        EcoRI

GTGTTGCGGGAACTGCGGTGCTGTGTTACAGACCACCGCAGGGAGTTCATCCC
        ValLeuArgGluLeuArgCysValCysLeuGlnThrThrGlnGlyValHisPro

AAAATGATCAGTAATCTGCAAGTGTTCGCCATAGGCCCACAGTGCTCCAAGGTGGAAGTG
LysMetIleSerAsnLeuGlnValPheAlaIleGlyProGlnCysSerLysValGluVal

GTAGCCTCCCTGAAGAACGGGAAGGAAATTTGTCTTGATCCAGAAGCCCCTTTTCTAAAG
ValAlaSerLeuLysAsnGlyLysGluIleCysLeuAspProGluAlaProPheLeuLys

5'
                        TADRAICTRCCICCITTRTTYCTYTTIcctaggat
                                                    BamHI
AAAGTCATCCAGAAAATCCTCGACGGCGGCAACAAAGAAAAC
LysValIleGlnLysIleLeuAspGlyGlyAsnLysGluAsn I=Inosine; R=A & G; Y=C & T; D=G, A & T; S=A & C
```

FIG. 9

```
         ENA-78   AGPAAAVLRELRCVCLQTTQ-GVHPKMISNLQ
         IL-8     SAKELRCQCIKTYSKPFHPKFIKELR
         NAP-2    AELRCMCIKTTS-GIHPKNIQSLE
         GROα     ASVATELRCQCLQTLQ-GIHPKNIQSVN
         GROβ     .PL.......L...L..K
         GROγ     ..V........L....
         PF-4     EAEEDGDLQCLCVKTTS-QVRPRHITSLE
         γIP-10   VPLSRTVRCTCISINQ-PVNPRSLEKLE

ENA-78   VFAIGPQCSKVEVVASLKN-GKEICLDPEAPFLKKVIQKILDGGNKEN
         IL-8     VIESGPHCANTEIIVKLSD-GRELCLDPKENWVQRVVEKFLKRAENS
         NAP-2    VIGKGTHCNQVEVIATLKD-GRKICLDPDAPRIKKIVQKKLAGDESAD
         GROα     VKSPGPHCAQTEVIATLKN-GRKACLNPASPIV..KKIIEKMLNSDKSN
         GROβ     ..............Q....M......Q......KNG..
         GROγ     .R............I....K.....M.Q.....LYKKIIKLLES.I.KGST.
         PF-4     VIKAGPHCPTAQLIATLKN-GRKICLDLQAPLYKKIIKLLES
         γIP-10   IIPASQFCPRVEIIATMKKGEKRCLNPESKAIKNLLKAVSKEMSKRSP
```

DNA ENCODING ENA-78, A NEUTROPHIL ACTIVATING FACTOR

BACKGROUND OF THE INVENTION

Neutrophil activation and chemotaxis have recently acquired increased attention through the discovery of the potent neutrophil activating peptide 1/interleukin-8 (IL-8), Walz, A. et al., *Biochem. Biophys. Res. Commun.* 149:755 (1987), Schroder, J. M. et al., *Immunol.* 139:3474 (1987), Yoshimura, T. et al., *Proc. Natl. Acad. Sci. U.S.A.* 84:9233 (1987) and Baggiolini, M. et al., *J. Clin. Invest.* 84:1045 (1989). Subsequently, two structural homologues with similar biological activities on human neutrophils were detected, neutrophil-activating peptide 2 (NAP-2), which is formed by proteolytic processing from platelet basic protein (PBP) or connective-tissue activating peptide III (CTAP-III) released from platelet α-granules, Walz, A. and M. Baggiolini, *Biochem. Biophys. Res. Commun.* 159:969 (1989) and Walz, A. and M. Baggiolini, *J. Exp. Med.* 171:449 (1990), and GROα, which was originally described as a mitogen for human melanoma cells, Richmond, A. et al., *EMBO J.* 7:2025 (1988) and was subsequently shown to activate neutrophils, Moser, B. et al., *J. Exp. Med.* 171:1797 (1990) and Schröder, J.-M. et al., *J. Exp. Med.* 171:1091 (1990). IL-8, NAP-2 and GROα belong to a family of peptides with a molecular weight of 8–10 kD, containing four conserved cysteine residues, the first two spaced by one amino acid (CXC). Two other members of this family are platelet factor 4 (PF-4) and γ-interferon inducible peptide 10 (γIP-10) Deuel, T. F. et al., *Proc. Natl. Acad. Sci. U.S.A.* 74:2256 (1977) and Luster, A. D. and J. V. Ravetch, *J. Exp. Med.* 166:1084 (1987).

Whereas the formation of NAP-2 is probably limited to the vascular system, IL-8 and GROα were shown to be secreted by a wide variety of cells. This and the demonstration of their in vivo chemotactic activity strongly supports their involvement in a number of inflammatory processes through the triggering of neutrophil infiltration and activation.

Neutrophil infiltration into the alveolar space is prominent in a variety of acute and chronic pulmonary inflammatory disorders. Alveolar macrophages, Rankin, J. A. et al., *J. Clin. Invest.* 86:1556 (1990) and Strieter, R. M. et al., *Am. J. Respir. Cell Mol. Biol.* 2:321 (1990) as well as lung epithelial cells, Standiford, T. J. et al., *J. Clin. Invest.* 86:1945 (1990) and fibroblasts, Golds, E. E. et al., *Biochem. J.* 259:585 (1989) have been shown to produce IL-8 in response to stimulation. IL-8 is also released by endothelial cells, which, like macrophages respond to LPS in addition to IL-1 and TNFα, Strieter, R. M. et al., *Science* 243:1467 (1989). Lung fibroblasts were shown to produce GROα in addition to IL-8 when stimulated with inflammatory cytokines, Golds, E. E. et al., *Biochem. J.* 259:585 (1989).

Since the pulmonary alveolus is in direct contact with the external environment, the alveolar macrophage might be the primary target of exogenous stimuli, such as viruses or bacterial products, which induce the expression of proinflammatory cytokines such as IL-1 and TNFα.

Type II alveolar cells appear to have a prominent role in the generation of neutrophil attractants. Here we describe the isolation and complete primary structure of a novel neutrophil activating peptide (ENA-78) from the human type II epithelial cell line A549.

SUMMARY OF THE INVENTION

The present invention is drawn to polypeptides having neutrophil stimulating activity. Preferably, such a factor comprises a polypeptide denominated ENA-78, said factor being from epithelial cells and having the ability to activate neutrophils. Preferably, such factors are derived from human epithelial cells, most preferably from the epithelial cell line A549.

Another aspect of the present invention comprises various fragments or variations of the naturally occurring factors having neutrophil stimulating activity. Preferably such variations will contain preferred portions of the amino terminal and/or carboxyl terminal amino acid sequence.

Another aspect of the present invention is DNA sequences coding for the polypeptides of the present invention, including the various fragments thereof. Preferred DNA sequences are those corresponding to the naturally occurring polypeptides having neutrophil stimulating activity and to the preferred polypeptide fragments of the present invention. Most preferably, the DNA sequence is that sequence of nucleotides corresponding to the coding region of FIG. 5a.

Another aspect of the present invention relates to a method of treating neutrophil deficiency comprising administering a neutrophil activating effective amount of a pharmaceutical composition comprising a polypeptide having neutrophil stimulating activity.

Another aspect of the present invention is a method for identifying inhibitors of polypeptides having neutrophil stimulating activity comprising:

A. culturing neutrophils in the presence of a candidate inhibitor;

B. adding a polypeptide having neutrophil stimulating activity;

C. comparing activation of neutrophils in step B to a culture of neutrophils in the presence of only a polypeptide having neutrophil stimulating activity. Preferably, the method will identify inhibitors to the polypeptide denominated ENA-78.

Another aspect of the present invention is the polypeptide inhibitors identified by the method for identifying inhibitors aspect of the present invention.

Another aspect of the present invention is a method for treating acute and chronic lung disorders in a mammal characterized by the presence of high numbers of neutrophils comprising administering neutrophil activating inhibitory effective amount of an inhibitor of the present invention. Preferably, the inhibitors will be used to treat disorders selected from the group consisting of adult respiratory distress syndrome, idiopathic pulmonary fibrosis and asbestosis.

DESCRIPTION OF THE FIGURES

FIGS. 2A, 2B, 2C, and 2D show (a) separation of neutrophil-stimulating activities from supernatants of IL-1β stimulated A549 cells by reversed-phase HPLC on a CN-propyl column. Three pools of activity (P1-P3) were collected and purified separately by reversed-phase HPLC on an analytical C4 column: (b) pool P1, (c) pool P2, (d) pool P3.

FIG. 4 shows amino acid partial sequences (Seq. ID No. 2 and Seq. ID No. 4) of neutrophil-activating peptides isolated from A549 cells (Seq. ID Nos. 2, 4, 13–15). Underlined sequences were used for reversed translation and construction of sense and antisense primers for the first strand synthesis and subsequent polymerase chain reaction.

FIG. 5A shows partial amino acid sequence (Seq. ID No. 9) of ENA-78 as determined by oligonucleotide primed synthesis of cDNA isolated from A549 cells. Mixtures of degenerated sense primer, encoding amino acid 7–17 (Seq. ID No. 10), and antisense primer, encoding amino acid 70–78 (Seq. ID No. 11) were used for the polymerase chain reaction (PCR). Nucleotide sequences of three individual cDNAs cloned in pTZ18R from the 226 bp band (see 6).

FIG. 9 shows amino acid sequences of ENA-78 (Seq. ID No. 12) and related peptides aligned according to their four cysteine residues (bold) (Seq. ID Nos. 16–22). For GROβ and GROγ only amino acids that differ from GROα are shown.

DETAILED DESCRIPTION OF THE INVENTION

Figure 1A:
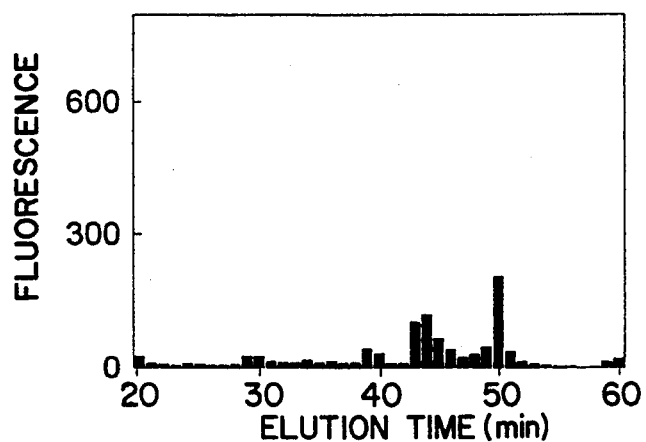
FIGS. 1A, 1B, 1C, and 1D show reversed-phase HPLC of neutrophil-activating peptides released by A549 cells. The cells were cultured for 24 h in medium without addition (a) or in the presence of 1 ug/ml LPS (b), 10 ng/ml IL-1β (c), or 20 ng/ml TNFα (d). The culture supernatants were collected and fractionated by cation-exchange chromatography on phosphocellulose, followed by reversed-phase HPLC on a CN-propyl column. The graphs show neutrophil-stimulating activity (elastase release from cytochalasin B treated human neutrophils) versus elution time on HPLC.
Figure 1B:
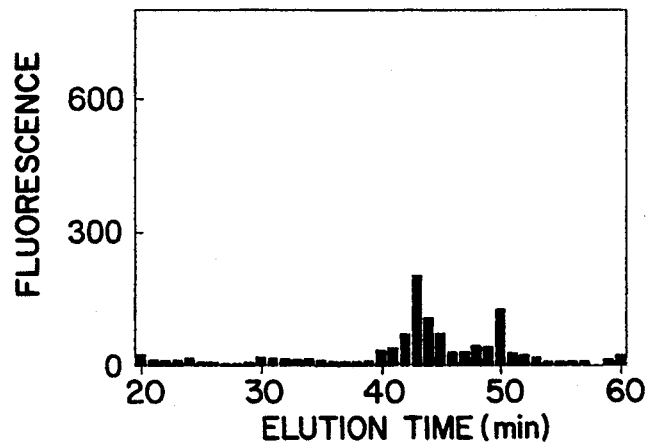
Figure 1C:
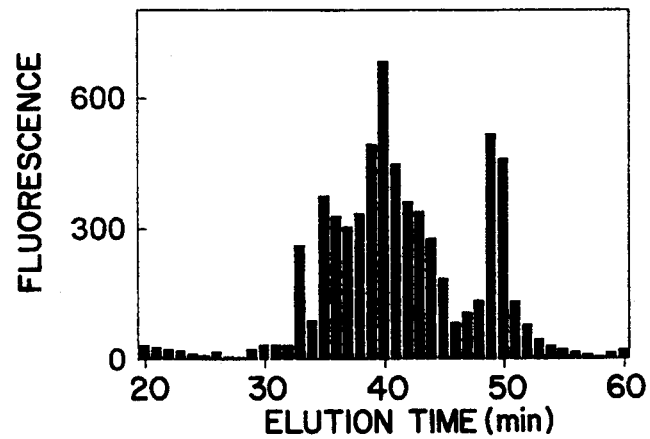
Figure 1D:
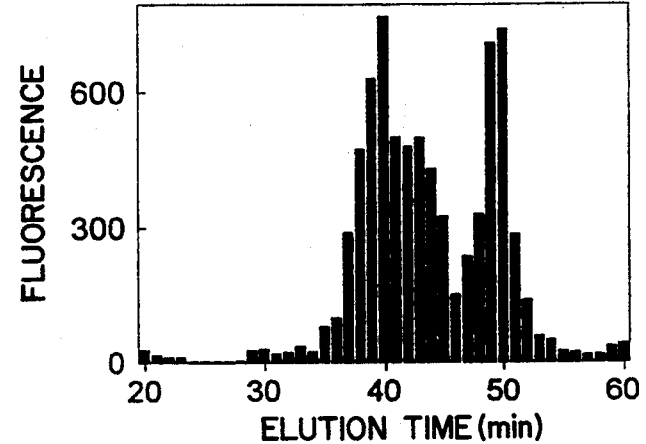

The present invention relates to a factor comprising a polypeptide denominated ENA-78, said factor being from epithelial cells and having the ability to activate neutrophils.

Such a factor can be obtained in a variety of ways. One way is to purify the factor from cells containing it. Epithelial cells, preferably human type II cells and more preferably the human type II epithelial cell line A549 are good sources of such factors. Examples of human type II cells include kidney and lung cells, preferably lung cells, most preferably the human type II epithelial cell line A549. The human type II epithelial cell line A549 can be obtained from the American Type Culture Collection, Rockville, Md. (ATCC Accession Number CCL 185). To enhance production of the desired neutrophil activating polypeptides, cells producing them can be stimulated with various cytokines, such as lipopolysaccharide (LPS, most preferably for 24 hours at a concentration of 1 μg/ml), tumor necrosis factor alpha (TNFα, most preferably for 24 hours at a concentration of 20 ng/ml) and interleukin-1beta (IL-1β, most preferably for 24 hours at a concentration of 10 ng/ml).

A factor according to the present invention can be purified from the appropriate cells by any of a number of acceptable methods which are known in the art. For example, ligands which bind the factor can be used in an affinity chromatography column. Such ligands include antibodies to the polypeptide, including monoclonal antibodies, as well as purified receptors that have the ability to bind the polypeptides.

A preferred method of purifying the factors comprises exposure of cell culture supernatants to phosphocellulose, followed by sequential purification using reverse phase chromatography, followed by several passes through high performance liquid chromatography (HPLC).

The most preferred method of purifying polypeptides of the present invention is as follows. First, dilute serum-free culture supernatants (450 ml) from the A549 pulmonary epithelial cells with one volume of loading buffer (20 mM KHPO4, pH 7.2, 20 mM NaCl, 5% glycerol), and load onto a 12 ml phosphocellulose column (Whatman P11) equilibrated with loading buffer. The column can be washed with the same buffer containing 200 mM NaCl and then eluted with buffer containing 1M NaCl (24 ml/min). Active fractions can then be pooled and further purified by repeated runs on a widepore analytical reversed-phase cyanopropyl column (4.6×250 mm, Baker Research Products) which can be eluted at 0.5 ml/min with a linear gradient of 0 to 50% acetonitrile in 0.1% trifluoroacetic acid (TFA) (0.83% increment per min). Pooled active fractions can be dried in a Speed-Vac centrifuge, resuspended in 0.1% TFA and further purified on a C4 reversed-phase column (4.6×250 mm, Baker Research Products) which was eluted at 0.5 ml/min with a linear gradient of 0 to 63% acetonitrile in 0.1% TFA (0.83% increment per min). Active fractions can then be rerun on a narrow-bore C4 column (2.1×100 mm, 7 um, Brownlee/Applied Biosystems) which was eluted at 0.3 ml/min with a linear gradient of 0 to 63% acetonitrile in 0.1% TFA (0.84% increment per min). Preferably, after this treatment, the activity will elute on HPLC into a broad peak with a retention time extending between 35 and 45 min, and a sharper peak eluting after 49 minutes. Only minor activity would be recovered in the supernatants of unstimulated or LPS-stimulated cells.

For purification and sequence analysis, liter quantities of conditioned medium from IL-1β and TNFα treated cultures are most preferably fractionated. HPLC on a CN-propyl column preferably yields three well-resolved peaks of activity (P1-P3) with mean retention times of 29, 35.8 and 48.1 min (FIG. 2a). These peak fractions can be pooled, dried and rechromatographed individually on a reversed-phase C4 column. Fraction P1 preferably separates into 3 activity peaks with retention times 50.2, 53.3 and 55.5 min (FIG. 2b). UREA-SDS-polyacrylamide gel electrophoresis most preferably yields single bands with apparent molecular weights corresponding to that of IL-8.

Candidate neutrophil activating polypeptides of the present invention can be analyzed throughout the purification procedure for their ability to stimulate neutrophils (neutrophil stimulating activity). Neutrophil activation can be measured, for example, as the capacity to induce release of elastase from human neutrophils pretreated with cytochalasin B [Peveri et al., J. Exp. Med. 167:1547 (1988); Dewald and Baggiolini, Biochem. Pharmacol. 36:2505–2510 (1987)] or by measuring cytosolic free calcium changes [Grynkiewicz, et al., J. Biol Chem. 260:3440 (1985)].

Another measurement of neutrophil stimulating activity is neutrophil migration, which can be measured in multiwell chemotaxis chambers [Leonard et al., J. Leukocyte Biol. 49:258 (1991)]. Preferably, the method of Leonard et al. is modified as follows. Dilutions of chemoattractants are loaded into the bottom wells in triplicates in prewarmed (37° C.) MEM supplemented with 0.2% bovine serum albumin (BS) and the chambers (also prewarmed) are assembled with a 5 um-pore diameter polyvinylpyrrolidone-free polycarbonate membrane (Nucleopore, Neuroprobe, Cabin John, Md.) Freshly isolated human neutrophils are placed into the upper wells (25,000 cells per well in 50 ul of MEM supplemented with 0.2% BSA) and chambers incubated at 37° C. for 1 h in humidified air with 5% $CO_2$. The polycarbonate filters are then removed and the cells on the upper surface are wiped off. After air-drying, the filters are stained with DADE Diff-Quik (Merz & Dade AG, Düdingen, Switzerland). Migrated cells are counted microscopically at 1000× magnification in 5 randomly chosen fields per well (0.03 mm$^2$/field of 3.17 mm$^2$ total area per well).

Candidate neutrophil activating polypeptides of the present invention can also be further analyzed for amino acid sequence. Amino acid sequences can be determined using automated protein sequencers such as those available from Applied Biosystems, Inc., particularly model 477A [Applied Biosystems, Inc., Foster City, Calif.; Hewick et al., J. Biol. Chem. 256:7990–7997 (1981); and Walz and Baggiolini Biochem. Biophys. Res. Comm. 159:969 (1989)]. Alternatively, sequencing of amino acids can be accomplished by sequential manual determination of the amino terminal amino acid [Edman and Begg, Eur. J. Biochem. !:80–91 (1967)]. Such amino acid sequencing techniques have provided an amino acid sequence for one neutrophil activating factor which is essentially the sequence of FIG. 5a.

Therefore, a preferred polypeptide of the present invention will have a C-terminal amino acid sequence (Seq. ID No. 1) of -Ile-Leu-Asp-Gly-Gly-Asn-Lys-Glu-Asn.

More preferably, the C-terminal amino acid sequence will be (Seq. ID No. 2)

—Asp—Pro—Glu—Ala—Pro—Phe—Leu—Lys—Lys—Val—Ile—Gln—Lys—Ile—Leu—Asp—Gly—Gly—Asn—Lys—Glu—Asn

Another preferred polypeptide of the present invention will have an N-terminal amino acid sequence (Seq. ID No. 3) of Ala—Gly—Pro—Ala—Ala—Ala—Val—Leu—Arg—Glu—Leu—Arg—Cys—Val—Cys—Leu—Gln—.

More preferably, the N-terminal amino acid sequence will be (Seq. ID No. 4)

Ala—Gly—Pro—Ala—Ala—Ala—Val—Leu—Arg—Glu—Leu—Arg—Cys—Val—Cys—Leu—Gln—Thr—Thr—Gln—Gly—Val—His—Pro—Lys—Met—Ile—Ser—Asn—Leu—Gln—Val—Phe—Ala—.

A very preferred polypeptide of the present invention has both a preferred C-terminal amino acid sequence and a preferred N-terminal amino acid sequence.

Preferred polypeptides of the present invention also include peptides having a truncated N-terminus. Particularly preferred truncated polypeptides include those wherein 6, 8, 9, 10, 11, or 12 amino acids have been deleted from the N-terminal end of the polypeptide depicted in FIG. 5a (Seq. ID No. 9), or any polypeptide that has substantial sequence homology to the polypeptide depicted in FIG. 5a (Seq. ID No. 9).

The present invention contemplates polypeptides having the sequence or fragments of the sequence of amino acids of FIG. 5a (Seq. ID No. 9) as well as polypeptides having substantial sequence homology. Substantial sequence homology means substantial functional and/or structural equivalence between sequences of nucleotides or amino acids. Functional and/or structural differences between sequences having substantial sequence homology will be de minimus. The sequences that differ from the natural sequences are usually variants of the natural sequence. A variant of a natural sequence is a modified form of the natural sequence that performs the same function. The variant may be a mutation, or may be a synthetic sequence. A de minimus functional difference results from a nucleotide or amino acid sequence that codes for a protein having essentially the same characteristics as the native protein. Such characteristics can include, for example, immunological reactivity, enzyme activity, structural protein integrity etc., preferably neutrophil stimulating activity. Structural differences are considered de minimus if there is a significant amount of sequence overlap or similarity between two or more different sequences or if the different sequences exhibit similar physical properties. In the case of a nucleotide sequence, the different sequences will preferably have at least 50 percent, more preferably 70 percent, most preferably 90 percent or more sequence similarity between them. In the case of amino acid sequences, the different sequences have at least 60 percent, preferably 70 percent, more preferably 80 percent, and most preferably 90 percent or more similarity between the polypeptides coded for by the amino acid sequences. Physical properties that may be similar include, for example, electrophoretic mobility, chromatography similarities, sediment gradient coefficients, spectrophotometric properties, etc.

The present invention also comprises DNA sequences that are capable of coding for proteins having neutrophil stimulating activity. Such DNA sequences may be obtained using standard procedures once the protein of interest has been isolated and an activity profile determined for it. For example, cells which are known to produce the protein can be used as a source of RNA. Total cellular RNA can be isolated using, for example, the method of Chirgwin et al. *Biochemistry* 18: 5294 (1979) and Jonas, E. et al., *Proc. Natl. Acad. Sci. USA* 82:5413 (1985). Preferably, the following modifications are made to the published method. A549 monolayers are scraped into a solution of 25 mM Tris/HCl, pH 8.0, containing 4.2M guanidine isothiocyanate, 0.5% sarcosyl and 100 mM 2-mercaptoethanol. After homogenization, an equal volume of 100 mM Tris/HCl, pH 8.0, containing 10 mM EDTA and 1% sodium dodecyl sulfate is added, and the mixture is extracted twice with chloroform-phenol and chloroform-isoamyl alcohol. The RNA is precipitated with isopropyl alcohol, washed with 80% ethanol in diethylpyrocarbonate-treated water (DEPC-water), and the pellet dissolved in DEPC-water. Poly(A) RNA can then be isolated by two passages on an oligo(dT)-cellulose column.

The poly(A) RNA can then be used to generate a cDNA. First, using random primers made to correspond to amino acids of the amino acid sequence, a cDNA strand can be generated in the presence of reverse transcriptase. After separation of the strands, double stranded DNA can be made using the polymerase chain reaction (PCR) with appropriate antisense and sense primers. After treatment with convenient restriction enzymes, the DNA can be cloned into a plasmid and transfected into an appropriate host for expression of proteins having neutrophil stimulating activity. Successful expression can be measured by assaying for neutrophil stimulating activity with the methods previously described.

Suitable random primers are at least six nucleotides in length, with those of six nucleotides in length being preferred. Suitable antisense primers are at least 14 nucleotides long, preferably 16 or more nucleotides long, most preferably about 16 nucleotides long. A most preferred method of first strand synthesis can be carried out in a total volume of 40 ul in the presence of 0.5 ug random hexamer primer or anti sense primer, preferably 4.2 ug ENA-78 antisense primer (FIG. 5a, Seq. ID No. 10 and Seq. ID No. 11), 2 ug of poly(A) RNA, 40 units RNAsin (Promega Biotec Inc.), 1 mM each of dNTPs, 400 units of MMLV reverse transcriptase (Bethesda Research Laboratories) and 8 ul of 5× RT-buffer (250 mM Tris/HCl, pH 8.3, 375 mM KCl, 15 mM MgCl$_2$, 50 mM DTT). This reaction mixture is then incubated for a suitable period of time, most preferably for about 2 h at about 37° C.

Preferably, PCR reactions can be carried out on the first strand cDNA in 50 ul containing 4 ul of 10× PCR buffer (500 mM KCl, 100 mM Tris/HCl, pH 8.3, 15 mM MgCl$_2$ and 0.01% gelatin), 10 ul first strand reaction, 3 ug of ENA-78 antisense primer, 4.5 ug of ENA-78 sense-primer (FIG. 5a, Seq. ID No. 10 and Seq. ID No. 11), 1 unit Taq polymerase (Perkin-Elmer/Cetus). The PCR can be run for 35 cycles (40 sec at 95° C., 90 sec at 55° C., 90 sec at 72° C.) in a Techne PHC-2 Thermocycler. The final product is then preferably extracted three times with phenol/chloroform and four times with ether. The DNA can then be precipitated with 0.3M Na-acetate and 2.5 volumes of ethanol. The PCR fragment produced with random hexamer primed cDNA is then isolated from the gel and can be cloned into a suitable plasmid, preferably plasmid pTZ18R. This plasmid can then be transfected into a suitable host, e.g., *E coli* HB101. Methods of transfection are known in the art and include electroporation, Ca-Phosphate, microinjection, etc.

The DNA sequences of the present invention include all DNA sequences that are capable of coding for proteins having neutrophil stimulating activity. This includes various fragments of the sequences, which code for the full length polypeptides.

A preferred DNA sequence of the present invention is essentially the sequence of FIG. 5a (Seq. ID No. 9). Another preferred DNA sequence of the present invention will have a 3' DNA sequence that codes for an amino acid sequence of Ile-Leu-Asp-Gly-Gly-Asn-Lys-Glu-Asn.

More preferably, the 3' DNA sequence will code for an amino acid sequence of

—Asp—Pro—Glu—Ala—Pro—Phe—Leu—Lys—Lys—Val—
Ile—Gln—Lys—Ile—Leu—Asp—Gly—Gly—Asn—Lys—
Glu—Asn.

Most preferably, the 3' DNA sequence will be (Seq. ID No. 5)

ATC CTC GAC GGC GGC AAC AAA GAA
AAC or (Seq. ID No. 6)

GAT CCA GAA GCC CCT TTT CTA AAG AAA GTC
ATC CAG AAA ATC CTC GAC GGC GGC AAC AAA
GAA AAC.

Another preferred DNA sequence of the present invention will have a 5' DNA sequence that codes for an amino acid sequence of Ala—Gly—Pro—Ala—Ala—Ala—Val—Leu—Arg—Glu—
Leu—Arg—Cys—Val—Cys—Leu—Gln—.

More preferably, the 5' DNA sequence will code for an amino acid sequence of

Ala—Gly—Pro—Ala—Ala—Ala—Val—Leu—Arg—Glu—
Leu—Arg—Cys—Val—Cys—Leu—Gln—Thr—Thr—Gln—
Gly—Val—His—Pro—Lys—Met—Ile—Ser—Asn—Leu—
Gln—Val—Phe—Ala.

Most preferably, the 5' DNA sequence will be (Seq. ID No. 7)

XXX XXX XXX XXX XXX XXX GTG TTG CGG GAA
CTG CGG TGC GTG TGT TTA CAG or (Seq. ID No. 8)

XXX XXX XXX XXX XXX XXX GTG TTG CGG GAA
CTG CGG TGC GTG TGT TTA CAG ACC ACG CAG
GGA GTT CAT CCC AAA ATG ATC AGT AAT CTG
CAA GTG TTC GCC, wherein X is selected from A, T, C and G. A very preferred DNA sequence of the present invention has both a preferred 3' DNA sequence and a preferred 5' DNA sequence.

Preferred DNA sequences of the present invention also include DNA sequences coding for peptides having a truncated N-terminus. Particularly preferred truncated DNA sequences include those DNA sequences coding for polypeptides wherein 6, 8, 9, 10, 11, or 12 amino acids have been deleted from the N-terminal end of the polypeptide depicted in FIG. 5a (Seq. ID No. 9 ), or any polypeptide that has substantial sequence homology to the polypeptide depicted in FIG. 5a (Seq. ID No. 9).

The DNA sequences of the present invention are useful for producing the polypeptides of the present invention. The DNA sequences can be cloned into an appropriate vector, such as a plasmid and introduced into a suitable expression host using standard transformation and transfection techniques. The selection of a suitable vector and host for a given polypeptide will depend on various factors, including the expression level desired, post translational modification of the polypeptide, glycosylation, location of the expressed polypeptide (secreted or membrane bound), etc.

The polypeptides of the present invention are useful in treating neutrophil deficient states in mammals, preferably humans. Polypeptides having neutrophil stimulating activity, such as ENA-78, are thus indicated for use in the treatment of conditions which are accompanied or caused, locally or systemically, by a modification of the number or activation state of the PMN (polymorphonuclear cells—neutrophils). The polypeptides extensively modify the PMN parameters and are therefore indicated for use in the treatment of conditions in which an increase of the number or enhancement of the activation state of the PMN leads to clinical improvement, e.g., in bacterial, mycoplasma, yeast, fungal, and in various vital infections. Furthermore, the polypeptides are indicated for use in inflammatory illnesses or in conditions of abnormally low neutrophil count and/or generalized low neutrophil level. The polypeptides can also be used in the treatment of hematopoietic deficits arising from chemotherapy or from radiation therapy. The success of bone marrow transplants may be enhanced by application of polypeptides having neutrophil stimulating activity. Wound healing burn treatment and the treatment of bacterial inflammation may also benefit from the application of polypeptides having neutrophil stimulating activity. The polypeptides of the present invention are also useful in the preparation of antagonists, e.g., monoclonal antibodies, inhibitors, etc.

Administration of the polypeptides of the present invention involves administration of an appropriate amount of a pharmaceutical composition containing the polypeptides as an active ingredient. In addition to the active ingredient, the pharmaceutical composition may also include appropriate buffers, diluents and additives. Appropriate buffers include, among others, Tris-HCl, acetate, glycine and phosphate, preferably phosphate at pH 6.5 to 7.5. Appropriate diluents include, among others, sterile aqueous solutions adjusted to isotonicity with NaCl, lactose or mannitol, preferably NaCl. Appropriate additives include among others, albumin or gelatin to prevent adsorption to surfaces, detergents (e.g., Tween 20, Tween 80, Pluronic F68), solubilizing agents (e.g., glycerol, polyethylene glycol), antioxidants (e.g., ascorbic acid, sodium metabisulfite) and preservatives (e.g., Thimersol, benzyl alcohol, parabens). A preferred additive is Tween 80.

Administration may be by any conventional means including intravenously, subcutaneously, or intramuscularly. The preferred route of administration is intravenous. Administration may be a single dose or may occur in an appropriate number of divided doses.

Preferably, the pharmaceutical preparation is in unit dosage form. In such form, the preparation is subdivided into unit doses containing the appropriate quantities of the active component, e.g., an effective amount to achieve the desired purpose.

The actual dosage employed may be varied depending upon the requirements of the patient and the severity of the condition being treated. Determination of the proper dosage for a particular situation is within the skill of the art. Generally, treatment is initiated with smaller dosages which are less than the optimum dose of the compound. Thereafter, the dosage is increased by small increments until the optimum effect under the circumstances is reached. For convenience, the total daily dosage may be divided and administered essentially continuously or in portions during the day if desired. The amount and frequency of administration will be regulated according to the judgment of the attending clinician considering such factors as age, condition and size of the patient as well as severity of the disease being treated.

A typical recommended dosage regime for use in the present invention is from about 0.1 to about 10 mg active ingredient per kg body weight per day.

The polypeptides of the present invention are also useful in the preparation of antagonists, e.g., monoclonal antibodies, inhibitors, etc., and preferably inhibitors. Such inhibitors can be identified using an assay based upon competitive binding and/or inhibition of the polypeptides having neutrophil stimulating activity. Such a method comprises:

A. culturing neutrophils in the presence of a candidate inhibitor;

B. adding a polypeptide having neutrophil stimulating activity;

C. comparing activation of neutrophils in step B to a culture of neutrophils in the presence of only a polypeptide having neutrophil stimulating activity.

The culture of neutrophils used can be any suitable culture of such polymorphonuclear cells. Preferably, the neutrophils are human neutrophils, which can be isolated for use in such an assay using the methods of Dewald and Baggiolini, *Methods in Enzymol.* 132: 267 (1986). The preferred neutrophils are freshly prepared before use by density centrifugation or Lymphoplaque (Pharmacia, Piscataway, N.J.). The neutrophils can be cultured in a suitable storage media. A particularly preferred storage media is 0.9% NaCl containing 50 $\mu$M CaCl$_2$. The storage media can also contain a candidate inhibitor in an amount sufficient to inhibit the neutrophil stimulating activity of a polypeptide having neutrophil stimulating activity. Added to the culture media, either before or after the addition of the candidate inhibitor, but preferably after, is a polypeptide having neutrophil stimulating activity. The preferred polypeptide having neutrophil stimulating activity is ENA-78, most preferably the polypeptide depicted in FIG. 5a (Seq. ID No. 9). Measurement of the neutrophil stimulating activity can then be measured using the methods previously described. The measurement of neutrophil stimulating activity in the presence of the candidate inhibitor, when compared to neutrophil stimulating activity in the absence of the candidate inhibitor will determine if the candidate inhibitor is indeed an inhibitor of the polypeptide having neutrophil stimulating activity.

The present invention is also drawn to the inhibitors of neutrophil activating polypeptides. Such inhibitors can be obtained from any number of sources. One preferred source is various modified versions of the naturally occurring polypeptides having neutrophil stimulating activity. Such modified versions include those polypeptides having substitutions, additions, and/or deletions of amino acids such that the modified polypeptide loses its ability to stimulate neutrophils and in fact became an inhibitor of polypeptides that do stimulate neutrophils. Substitutions, deletions or additions that occur in the region of the "active site" of the polypeptide having neutrophil stimulating activity are particularly suitable candidates for inhibitors.

The inhibitors of polypeptides having neutrophil stimulating activity are useful for treating disorders characterized by the presence of high numbers of neutrophils. Several acute and chronic lung disorders are characterized by the presence of high numbers of neutrophils. Such acute and chronic lung disorders include adult respiratory distress syndrome, idiopathic pulmonary fibrosis, asbestosis, and asthma. Treatment of such disorders comprises administering neutrophil activating inhibitory effective amount of an inhibitor of a polypeptide having neutrophil stimulating activity.

Formulation of the pharmaceutical composition for the inhibitors, as well as the administration of the pharmaceutical composition can be determined in the same manner used for the formulation and administration of the polypeptides having neutrophil stimulatory activity taking into account the different goal (inhibition rather than stimulation) to be achieved.

EXAMPLES

The following examples are intended to exemplify specific embodiments of the present invention without limiting the scope in any way.

Example 1

Obtaining ENA-78 Protein from Stimulated Pulmonary Epithelial Cells

Human recombinant IL-1β (30 units/ng), human recombinant TNFα (22 units/ng) and human recombinant IL-8, Lindley, I. et al., Proc. Natl. Acad. Sci. U.S.A. 859199 (1988) were kindly provided by Upjohn, Genentech and Sandoz, respectively. NAP-2 was purified as described previously, Walz, A. and M. Baggiolini, Biochem. Biophys. Res. Commun. 159:969 (1989). Synthetic oligonucleotides were prepared on a Applied Biosystems 391 DNA Synthesizer and desalted on NAP 10 columns (Pharmacia).

A549 pulmonary epithelial cells (American Type Culture Collection, Accession Number CCL 185) were grown to confluency in 225 cm² culture flasks (Costar) with complete RPMI 1640 (RPMI), plus 10% fetal calf serum (FCS). Confluent monolayers were washed free of FCS with RPMI and stimulated for 24 h with 1 ug/ml LPS, 20 ng/ml TNFα or 10 ng/ml IL-1β (300 ml RPMI per flask). Cell-free supernatants were then collected and stored at −75° C. Total cellular RNA was extracted from the monolayers as described below. Human neutrophils were isolated and used as described previously, Peveri, P. et al., J. Exp. Med. 167:1547 (1988).

Serum-free culture supernatants (450 ml) from the A549 pulmonary epithelial cells were diluted with one volume of loading buffer (20 mM KHPO$_4$, pH 7.2, 20 mM NaCl, 5% glycerol), and loaded onto a 12 ml phosphocellulose column (Whatman P11) equilibrated with loading buffer. The column was washed with the same buffer containing 200 mM NaCl and then eluted with buffer containing 1M NaCl (24 ml/min). Active fractions were pooled and further purified by repeated runs on a wide-pore analytical reversed-phase cyanopropyl column (4.6×250 mm, Baker Research Products) which was eluted at 0.5 ml/min with a linear gradient of 0 to 50% acetonitrile in 0.1% trifluoroacetic acid (TFA) (0.83% increment per min). Active fractions were pooled, dried in a Speed-Vac centrifuge, resuspended in 0.1% TFA and further purified on a C4 reversed-phase column (4.6×250 mm, Baker Research Products) which was eluted at 0.5 ml/min with a linear gradient of 0 to 63% acetonitrile in 0.1% TFA (0.83% increment per min). Active fractions were rerun on a narrow-bore C4 column (2.1×100 ram, 7 um, Brownlee/Applied Biosystems) which was eluted at 0.3 ml/min with a linear gradient of 0 to 63% acetonitrile in 0.1% TFA (0.84% increment per min).

As shown in FIGS. 1A–1D, stimulation of pulmonary epithelial cells by TNFα or IL-1β led to production and release of substantial amounts of neutrophil-activating peptides. On HPLC, the activity eluted into a broad peak with a retention time extending between 35 and 45 min, and a sharper peak eluting after 49 minutes. Only minor activity was recovered in the supernatants of unstimulated or LPS-stimulated cells.

Figure 3:
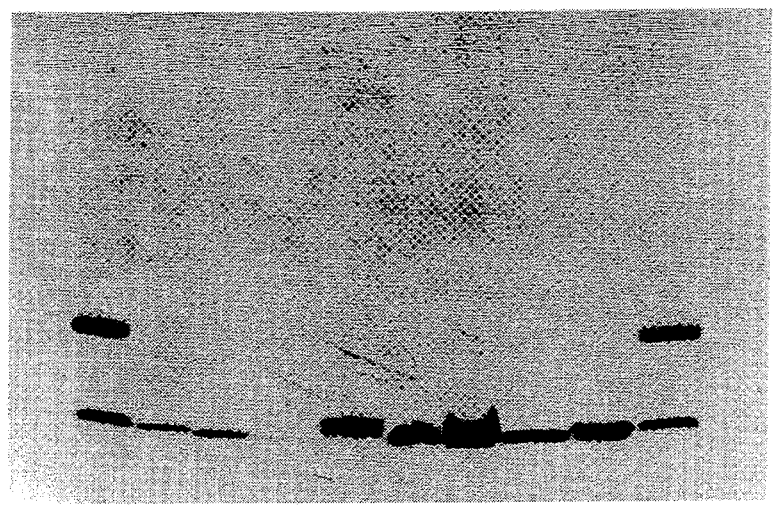
FIG. 3 shows UREA-SDS-polyacrylamide gel electrophoresis of purified neutrophil-activating peptides. Molecular weight markers aprotinin (6.5 kD) and lysozyme (14.4 kD) (Lane 1 and 10), active peptide from pool P1 (49.3 rain peak) (lane 2), GROα (lane 3), GROγ (lane 4), IL-8 (77) (lane 5), three preparations of ENA-78 (lane 6-8) and recombinant IL-8 (lane 9).

For purification and sequence analysis, liter quantities of conditioned medium from IL-1β and TNFα treated cultures were fractionated. HPLC on a CN-propyl column yielded three well-resolved peaks of activity (P1-P3) with mean retention times of 29, 35.8 and 48.1 min (FIG. 2a). The peak fractions were pooled, dried and rechromatographed individually on a reversed-phase C4 column. Fraction P1 separated into 3 activity peaks with retention times 50.2, 53.3 and 55.5 min (FIG. 2b). UREA-SDS-polyacrylamide gel electrophoresis yielded single bands with apparent molecular weights corresponding to that of IL-8 (FIG. 3). All three preparations were subjected to Edman degradation. No defined sequence could be determined in the material eluting at 50.2 min due to the presence of more than one peptide species, while the materials eluting at 53.3 and 55.5 min could be identified as GROα and GROγ, respectively, by sequencing the first 13 amino-terminal residues (FIG. 4). Fraction P2 yielded one single peak with biological activity that could be identified as the 77-amino acid form of IL-8 (FIG. 4) The 72-amino acid form of IL-8, the major product of monocytes, was not detected in the lung epithelial cell supernatants. Fraction P3 contained a novel peptide with considerable sequence homology to NAP-2 and GROα, but clearly less homology to IL-8.

Example 2

Structure of ENA-78 from Stimulated Pulmonary Epithelial Cells

Three separate preparations of P3 were analyzed. On UREA-SDS-polyacrylamide gels, they all yielded a single band with slightly higher motility than IL-8

(FIG. 3). Sequencing led to the identification of 34 amino-terminal and, after acid hydrolysis of the Asp57-Pro58 bond, 21 carboxy-terminal residues (FIG. 4). The remaining 22 residues were identified indirectly using PCR-methodology.

Isolation of poly(A) RNA. Total cellular RNA from A549 cells was isolated using a modification of the methods of Chirgwin et al., *Biochemistry* 18:5294 (1979) and Jonas, E. et al., *Proc. Natl. Acad. Sci. USA* 82:5413 (1985). Briefly, A549 monolayers were scraped into a solution of 25 mM Tris/HCl, pH 8.0, containing 4.2M guanidine isothiocyanate, 0.5% sarcosyl and 100 mM 2-mercaptoethanol. After homogenization, an equal volume of 100 mM Tris/HCl, pH 8.0, containing 10 mM EDTA and 1% sodium dodecyl sulfate was added, and the mixture was extracted twice with chloroform-phenol and chloroform-isoamyl alcohol. The RNA was precipitated with isopropyl alcohol, washed with 80% ethanol in diethylpyrocarbonate-treated water (DEPC-water), and the pellet dissolved in DEPC-water. Poly(A) RNA was then isolated by two passages on an oligo(dT)-cellulose column.

Preparation of cDNA. First strand synthesis was carried out in a total volume of 40 ul in the presence of 0.5 ug random hexamer primer or 4.2 ug ENA-78 antisense primer (FIG. 5a, Seq. ID No. 4), 2 ug of poly(A) RNA, 40 units RNAsin (Promega Biotec Inc.), 1 mM each of dNTPs, 400 units of MMLV reverse transcriptase (Bethesda Research Laboratories) and 8 ul of 5×RT-buffer (250 mM Tris/HCl, pH 8.3, 375 mM KCl, 15 mM $MgCl_2$, 50 mM DTT). This reaction mixture was incubated for 2 h at 37° C.

Figure 5B:
FIG. 5B shows gel electrophoretic analysis of the PCR products. Products of PCR amplifications were separated on a 5% NuSieve agarose gel and stained with ethidium bromide. Molecular size markers (lane 1), control PCR reaction, 234 bp (lane 2), PCR product obtained from A549 cDNA by random hexamer priming (lane 3), PCR product obtained from A549 cDNA by priming with antisense primer (lane 4), reaction mix without template (lane 5).

PCR reactions were carried out on the first strand cDNA in 50 ul containing 4 ul of 10×PCR buffer (500 mM KCl, 100 mM Tris/HCl, pH 8.3, 15 mM $MgCl_2$ and 0.01% gelatin), 10 ul first strand reaction, 3 ug of ENA-78 antisense primer, 4.5 ug of ENA-78 sense-primer (FIG. 5a), 1 unit Tag polymerase (Perkin-Elmer/Cetus). The PCR was run for 35 cycles (40 sec at 95° C., 90 sec at 55° C., 90 sec at 72° C.) in a Techne PHC-2 Thermocycler. The final product was extracted three times with phenol/chloroform and four times with ether. The DNA was then precipitated with 0.3M Na-acetate and 2.5 volumes of ethanol. The cDNA encoding amino acids 7 to 78 was amplified using sense and antisense primers and analyzed. PCR with antisense-primed cDNA yielded two prominent bands, the lower of which had the predicted size of about 235 bp (FIG. 5b). PCR with random hexamer primed cDNA yielded one single band of similar size (FIG. 5b). The latter fragment was isolated from the gel and cloned into plasmid pTZ18R. The PCR-product was resuspended in STE, restricted with EcoRI and BamHI, separated on a 5% NuSieve agarose gel in 40 mM Tris, 20 mM acetate, pH 8.0, 2 mM EDTA. DNA was visualized by staining with ethidium bromide, bands were cut out, electroeluted (Blotrap, Schleicher und Schuell) and ligated into plasmid pTZ18R (Pharmacia Biosystems). The construct was then transfected into *E coli* HB101 by electropotation (Biorad Gene Pulser) at 2.5 kV, 25 uF, 400 Ohm. A number of positive clones were analyzed for their inserted cDNA by DNA sequencing with Sequenase (United States Biochemical Corporation). Five clones were sequenced as follows. Amino acid sequence analysis was performed with an Applied Biosystems gas-phase sequencer Model 477A, Walz, A. and M. Baggiolini, *Biochem. Biophys. Res. Commun.* 129:969 (1989). Cleavage at the Asp-Pro bond of purified, unmodified ENA-78 was performed in 75% (vol/vol) formic acid at 37° C. for 60 h. The digestion mixture was then diluted four times with 0.1% TFA and loaded directly onto a narrow-bore reversed-phase C4 column as described above. Three contained the correct sequence between the primers, and two were also identical in the primer region (FIG. 5a).

These results show that ENA-78 consists of 78 amino acids. It has molecular weight of 8,357 daltons and a calculated isoelectric point of 8.73. The position of the four cysteine residues is identical as in the sequence of IL-8, strongly suggesting that ENA-78 belongs to the CXC family of inflammatory peptides. The amino-terminal sequence up to the first cysteine consists of 12 residues and approximately corresponds in length to that of the 77-residue form of IL-8 (FIG. 9, Seq. ID No. 12). No truncated variants of either peptide were detected. The sequence of ENA-78 contains two potential phosphorylation sites, one for casein kinase II at residue 40 (pqcSkve) and one for protein kinase C at residue 47 (vvaSlkn). No apparent sites for N-linked glycosylation are present. Sequence identities between ENA-78 (Seq. ID No. 12) and NAP-2 (Seq. ID No. 17), GROα (Seq. ID No. 18), PF-4 (Seq. ID No. 21), IL-8 (Seq. ID No. 16), and γIP-10 (Seq. ID No. 22) are 53, 52, 44, 22 and 15%, respectively.

Example 3

Measurement of Biological Activities for ENA-78

Neutrophil activation. Established methods were used to assess elastase release, Peveri, P. et al., *J. Exp. Med.* 167:1547 (1988) and cytosolic free calcium changes, Grynkiewicz, G. et al., *J. Biol. Chem.* 260:3440 (1985) in human neutrophils.

Figure 6:
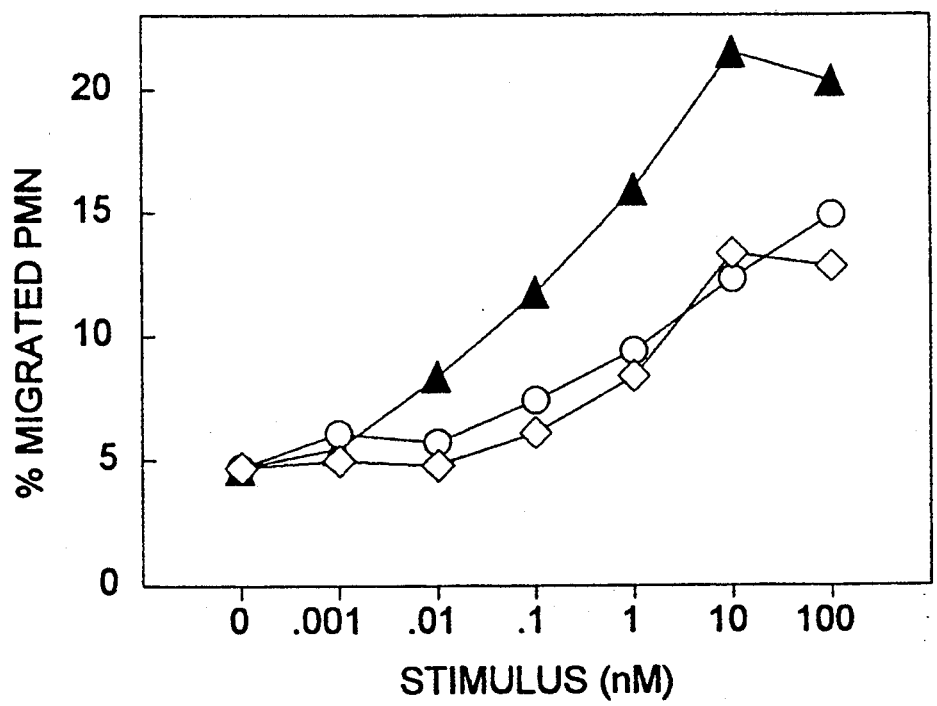
FIG. 6 shows human neutrophil chemotaxis induced by ENA-78 ( ), IL-8 ( ) and NAP-2 (O). The response was calculated as the % neutrophils of input number migrated to the lower side of the polycarbonate membrane. The results shown here are the mean of three independent experiments.

Neutrophil migration was determined in multiwell chemotaxis chambers (Neuroprobe Inc.), Leonard, E. J. et al., *J. Leukocyte Biol.* 49:258 (1991). Dilutions of chemoattractants were loaded into the bottom wells in triplicates in prewarmed (37° C.) MEM supplemented with 0.2% bovine serum albumin (BSA) and the chambers (also prewarmed) were assembled with a 5 um-pore diameter polyvinylpyrrolidone-free polycarbonate membrane (Nucleopore). Freshly isolated human neutrophils were placed into the upper wells (25,000 cells per well in 50 ul of MEM supplemented with 0.2% BSA) and chambers incubated at 37° C. for 1 h in humidified air with 5% $CO_2$. The polycarbonate filters were then removed and the cells on the upper surface were wiped off. After air-drying the filters were stained with DADE Diff-Quik (Metz & Dade AG, Düdingen, Switzerland). Migrated cells were counted microscopically at 1000× magnification in 5 randomly chosen fields per well (0.03 $mm^2$/field of 3.17 $mm^2$ total area per well). Each point in FIG. 6 represents the average of 3 independent experiments (15 fields per experiment).

Figure 7A:
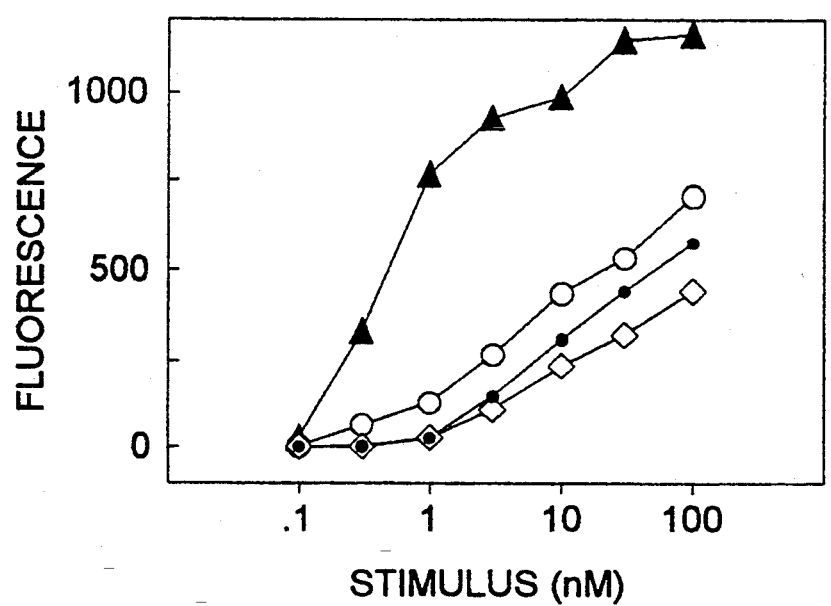
FIG. 7A and 7B show effects of ENA-78 on human neutrophils. (a) Release of elastase from cytochalasin B-treated cells s stimulated with two preparations of ENA-78 ( ), ·), IL-8 ( ) and NAP-2 (O). (b) Rate of cytosolic free calcium rise in cells stimulated with ENA-78 ( ) IL-8 ( ) and NAP-2 (O).

Biological activities. The effects of ENA-78 on neutrophils were studied in comparison with NAP-2 and IL-8. As shown in FIG. 6, ENA-78 induced a concentration-dependent migration response in vitro between 0.1 and 100 nM. NAP-2 was active in the same concentration range and showed a similar efficacy. The percentage of migrating cells at the maximum-effective concentration of 100 nM were 22, 15 and 13% for IL-8, NAP-2 and ENA-78, respectively (mean of 3 experiments). ENA-78 also induced the release of elastase from cytochalasin B-pretreated cells at concentrations ranging between 1 and 100 nM, as was the case for NAP-2 and IL-8. At 100 nM, IL-8 was consistently 2 to 3-fold more effective than NAP-2 and ENA-78 (FIG. 7a).

Figure 7B:
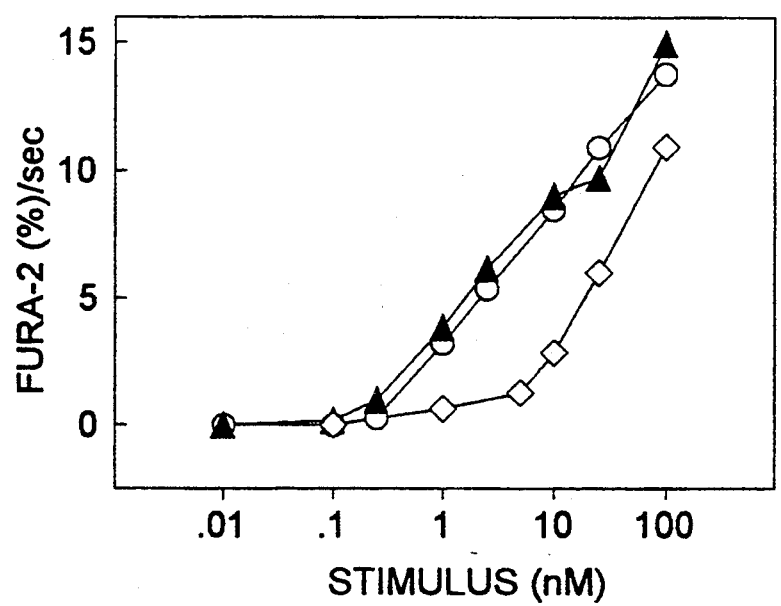
Figure 8A:
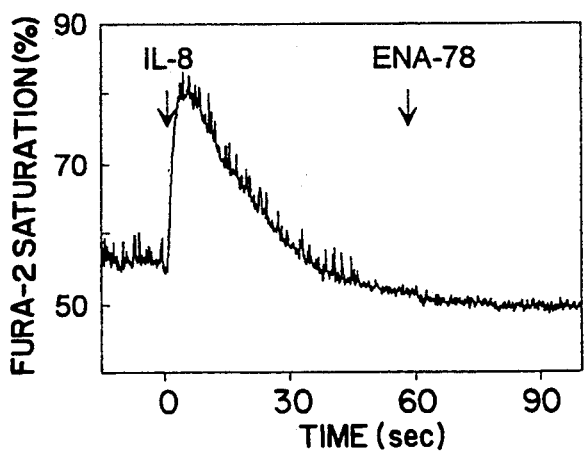
FIGS. 8 A, 8B, 8C, and 8D show cytosolic free calcium changes in response to sequential stimulation of human neutrophils with combinations of ENA-78, IL-8 and NAP-2 at 100 nM.
Figure 8B:
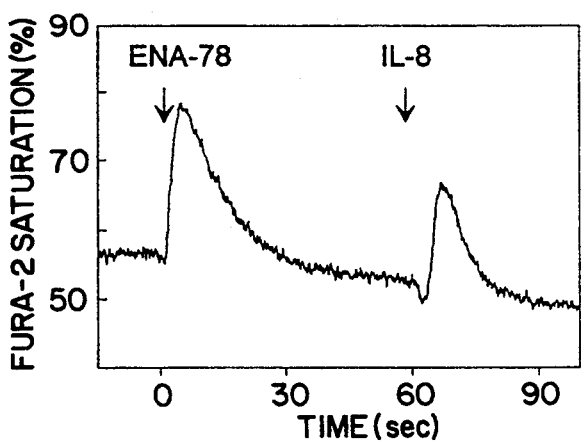
Figure 8C:
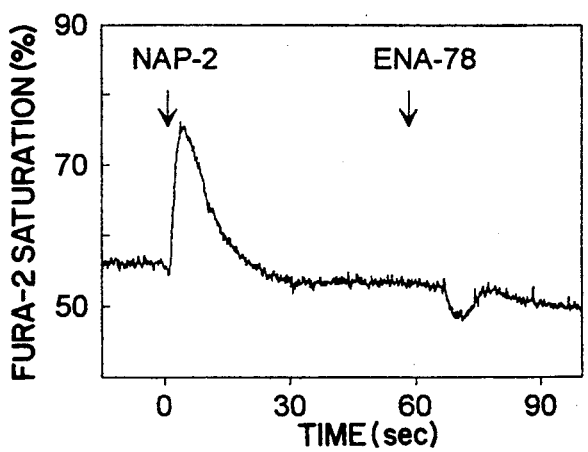
Figure 8D:
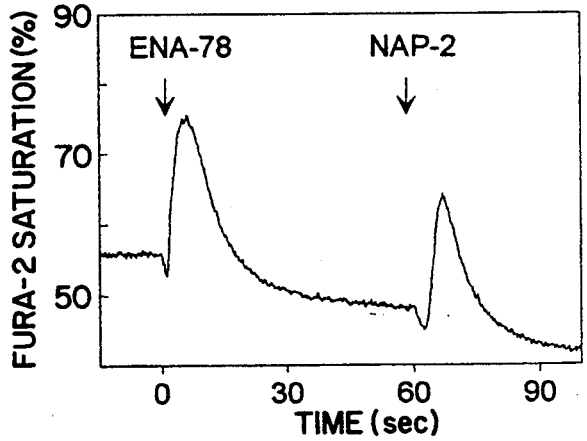

The somewhat lower potency of ENA-78 with respect to NAP-2 and IL-8 was also reflected by the measurements of stimulus-dependent changes in cytosolic free calcium. As illustrated in FIG. 7b, the curve relating the rate of the calcium rise with the agonist concentration was virtually identical for IL-8 and NAP-2, and displaced to the right for ENA-78. Half-maximal rates were reached at ENA-78 concentrations that were about 10-times higher than those required for the reference peptides.

[$Ca^{2+}$] changes in response to sequential stimulations with IL-8, NAP-2 and ENA-78 were studied to explore the possibility of functional interactions among these related agonists. Desensitization of the neutrophils were always observed whenever the same agonist was applied twice at the same concentration, as reported previously for IL-8, Peveri, P. et al., J. Exp. Med. 167: 1547 (1988) and Schroder, J. M. et al., J. Immunol. 140:3534 (1988). The results obtained upon sequential stimulation with combinations of the three agonists are shown in FIGS. 8A–8D. A first stimulation with 100 nM ENA-78 decreased only slightly the [$Ca^{2+}$]; rise induced by the subsequent stimulation with 100 nM IL-8 or NAP-2. By contrast, prestimulation with 100 nM IL-8 or NAP-2 abolished the response to the subsequent challenge with t00 nM ENA-78. These results suggest that ENA-78 activates neutrophils via the same or a closely-related receptor system as IL-8 and analogues.

Example 4

Assay for Inhibitory Activity of a Candidate Inhibitor

Neutrophils are loaded with Fura 2 as described by Walz et al., J. Leukocyte Biol. 50:270 (1991). Cytosolic free calcium changes are then measured in cuvettes containing 1 ml of buffer (136 mM NaCl, 4.8 mM KCl, 1 mM $CaCl_2$, 5 mM glucose, 20 mM HEPES, ph 7.4 and 310 mOsm) and $2 \times 10^6$ neutrophils. Candidate inhibitors are added at concentrations of approximately $10^{-5}$ to $10^{-9}$M, followed at various time intervals by an injection of a neutrophil-stimulating peptide (ENA-78, IL-8, NAP-2 or GROα) at $10^{-8}$ to $10^{-9}$M concentration. A candidate inhibitor will be considered as inhibitory to neutrophil stimulating activity if it does not induce a fluorescence signal by itself, but reduces or depresses the calcium flux normally observed with the subsequent addition of the neutrophil-stimulating peptide.

Similarly, using cytochalasin B-treated neutrophils, an inhibitory activity of a candidate inhibitor can be detected by a reduction or inhibition of elastase release from the azurophil granules. The candidate inhibitor can either be added to the neutrophils before the neutrophil stimulating peptides, or together, when the candidate inhibitor and the agonist were preincubated in the absence of cells for a certain time interval.

What is claimed is:

1. An isolated DNA sequence encoding a polypeptide consisting of amino acids 1–78 shown in SEQ ID NO: 12, said polypeptide having the ability to activate neutrophils.

2. A vector comprising a DNA sequence according to claim 1.

3. A host cell transformed by a vector according to claim 2.

4. An isolated DNA sequence encoding a polypeptide consisting of amino acids 1–72 shown in SEQ ID NO: 9, said polypeptide having the ability to activate neutrophils.

5. A vector comprising a DNA sequence according to claim 4.

6. A host cell transformed by a vector according to claim 5.

---

SEQUENCE LISTING ( 1 ) GENERAL INFORMATION:

( i i i ) NUMBER OF SEQUENCES: 22

( 2 ) INFORMATION FOR SEQ ID NO:1:

( i ) SEQUENCE CHARACTERISTICS:
( A ) LENGTH: 9
( B ) TYPE: Amino Acid
( D ) TOPOLOGY: Linear ( x i ) SEQUENCE DESCRIPTION: SEQ ID NO:1:

Ile  Leu  Asp  Gly  Gly  Asn  Lys  Glu  Asn
 1                 5

( 2 ) INFORMATION FOR SEQ ID NO:2:

( i ) SEQUENCE CHARACTERISTICS:
( A ) LENGTH: 22
( B ) TYPE: Amino Acid
( D ) TOPOLOGY: Linear ( x i ) SEQUENCE DESCRIPTION: SEQ ID NO:2:

Asp  Pro  Glu  Ala  Pro  Phe  Leu  Lys  Lys  Val  Ile  Gln  Lys  Ile  Leu
 1                 5                              10                              15

Asp  Gly  Gly  Asn  Lys  Glu  Asn
               2 0

( 2 ) INFORMATION FOR SEQ ID NO:3:

( i ) SEQUENCE CHARACTERISTICS:
        ( A ) LENGTH: 17
        ( B ) TYPE: Amino Acid
        ( D ) TOPOLOGY: Linear ( x i ) SEQUENCE DESCRIPTION: SEQ ID NO:3:

```
Ala  Gly  Pro  Ala  Ala  Ala  Val  Leu  Arg  Glu  Leu  Arg  Cys  Val  Cys
 1              5                        10                          15

Leu  Gln
     17
```

( 2 ) INFORMATION FOR SEQ ID NO:4:

( i ) SEQUENCE CHARACTERISTICS:
        ( A ) LENGTH: 34
        ( B ) TYPE: Amino Acid
        ( D ) TOPOLOGY: Linear ( x i ) SEQUENCE DESCRIPTION: SEQ ID NO:4:

```
Ala  Gly  Pro  Ala  Ala  Ala  Val  Leu  Arg  Glu  Leu  Arg  Cys  Val  Cys
 1              5                        10                          15

Leu  Gln  Thr  Thr  Gln  Gly  Val  His  Pro  Lys  Met  Ile  Ser  Asn  Leu
                20                        25                          30

Gln  Val  Phe  Ala
               34
```

( 2 ) INFORMATION FOR SEQ ID NO:5:

( i ) SEQUENCE CHARACTERISTICS:
        ( A ) LENGTH: 27
        ( B ) TYPE: Nucleic Acid
        ( C ) STRANDEDNESS: Single Stranded
        ( D ) TOPOLOGY: Linear ( x i ) SEQUENCE DESCRIPTION: SEQ ID NO:5:

```
ATCCTCGACG  GCGGCAACAA  AGAAAAC                                    27
```

( 2 ) INFORMATION FOR SEQ ID NO:6:

( i ) SEQUENCE CHARACTERISTICS:
        ( A ) LENGTH: 66
        ( B ) TYPE: Nucleic Acid
        ( C ) STRANDEDNESS: Single Stranded
        ( D ) TOPOLOGY: Linear ( x i ) SEQUENCE DESCRIPTION: SEQ ID NO:6:

```
GATCCAGAAG  CCCCTTTTCT  AAAGAAAGTC  ATCCAGAAAA  TCCTCGACGG         50

CGGCAACAAA  GAAAAC                                                 66
```

( 2 ) INFORMATION FOR SEQ ID NO:7:

( i ) SEQUENCE CHARACTERISTICS:
        ( A ) LENGTH: 51
        ( B ) TYPE: Nucleic Acid
        ( C ) STRANDEDNESS: Single Stranded
        ( D ) TOPOLOGY: Linear ( x i ) SEQUENCE DESCRIPTION: SEQ ID NO:7:

```
NNNNNNNNNN  NNNNNNNNGT  GTTGCGGGAA  CTGCGGTGCG  TGTGTTTACA         50

G                                                                  51
```

( 2 ) INFORMATION FOR SEQ ID NO:8:

(i) SEQUENCE CHARACTERISTICS:
    (A) LENGTH: 102
    (B) TYPE: Nucleic Acid
    (C) STRANDEDNESS: Single Stranded
    (D) TOPOLOGY: Linear (xi) SEQUENCE DESCRIPTION: SEQ ID NO:8:

```
NNNNNNNNNN NNNNNNNNGT GTTGCGGGAA CTGCGGTGCG TGTGTTTACA          50

GACCACGCAG GGAGTTCATC CCAAAATGAT CAGTAATCTG CAAGTGTTCG         100

CC                                                            102
```

(2) INFORMATION FOR SEQ ID NO:9:

(i) SEQUENCE CHARACTERISTICS:
    (A) LENGTH: 216
    (B) TYPE: Nucleic Acid
    (C) STRANDEDNESS: Single Stranded
    (D) TOPOLOGY: Linear (xi) SEQUENCE DESCRIPTION: SEQ ID NO:9:

```
GTG  TTG  CGG  GAA  CTG  CGG  TGC  GTG  TGT  TTA  CAG  ACC  ACG  CAG  GGA    45
Val  Leu  Arg  Glu  Leu  Arg  Cys  Val  Cys  Leu  Gln  Thr  Thr  Gln  Gly
 1             5                        10                        15

GTT  CAT  CCC  AAA  ATG  ATC  AGT  AAT  CTG  CAA  GTG  TTC  GCC  ATA  GGC    90
Val  His  Pro  Lys  Met  Ile  Ser  Asn  Leu  Gln  Val  Phe  Ala  Ile  Gly
                    20                       25                       30

CCA  CAG  TGC  TCC  AAG  GTG  GAA  GTG  GTA  GCC  TCC  CTG  AAG  AAC  GGG   135
Pro  Gln  Cys  Ser  Lys  Val  Glu  Val  Val  Ala  Ser  Leu  Lys  Asn  Gly
                     35                      40                       45

AAG  GAA  ATT  TGT  CTT  GAT  CCA  GAA  GCC  CCT  TTT  CTA  AAG  AAA  GTC   180
Lys  Glu  Ile  Cys  Leu  Asp  Pro  Glu  Ala  Pro  Phe  Leu  Lys  Lys  Val
                     50                      55                       60

ATC  CAG  AAA  ATC  CTC  GAC  GGC  GGC  AAC  AAA  GAA  AAC                  216
Ile  Gln  Lys  Ile  Leu  Asp  Gly  Gly  Asn  Lys  Glu  Asn
                     65                      70
```

(2) INFORMATION FOR SEQ ID NO:10:

(i) SEQUENCE CHARACTERISTICS:
    (A) LENGTH: 34
    (B) TYPE: Nucleic Acid
    (C) STRANDEDNESS: Single Stranded
    (D) TOPOLOGY: Linear (xi) SEQUENCE DESCRIPTION: SEQ ID NO:10:

```
TCGAATTCGT NYTNMGNGAA CTNMGNTGYG TNTG                          34
```

(2) INFORMATION FOR SEQ ID NO:11:

(i) SEQUENCE CHARACTERISTICS:
    (A) LENGTH: 35
    (B) TYPE: Nucleic Acid
    (C) STRANDEDNESS: Single Stranded
    (D) TOPOLOGY: Linear (xi) SEQUENCE DESCRIPTION: SEQ ID NO:11:

```
TAGGATCCNT TYTCYTTRTT NCCNCCRTCN ARDAT                         35
```

(2) INFORMATION FOR SEQ ID NO:12:

(i) SEQUENCE CHARACTERISTICS:
    (A) LENGTH: 78
    (B) TYPE: Amino Acid
    (D) TOPOLOGY: Linear (xi) SEQUENCE DESCRIPTION: SEQ ID NO:12:

```
Ala  Gly  Pro  Ala  Ala  Ala  Val  Leu  Arg  Glu  Leu  Arg  Cys  Val  Cys
```

|  1 |  |  | | 5 |  |  |  |  | 10 |  |  |  |  | 15 |
|---|---|---|---|---|---|---|---|---|---|---|---|---|---|---|

Leu Gln Thr Thr Gln Gly Val His Pro Lys Met Ile Ser Asn Leu
                    20                  25                  30

Gln Val Phe Ala Ile Gly Pro Gln Cys Ser Lys Val Glu Val Val
                    35                  40                  45

Ala Ser Leu Lys Asn Gly Lys Glu Ile Cys Leu Asp Pro Glu Ala
                    50                  55                  60

Pro Phe Leu Lys Lys Val Ile Gln Lys Ile Leu Asp Gly Gly Asn
                    65                  70                  75

Lys Glu Asn
        78

( 2 ) INFORMATION FOR SEQ ID NO:13:

( i ) SEQUENCE CHARACTERISTICS:
        ( A ) LENGTH: 13 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:13:

Ala Ser Val Ala Thr Glu Leu Arg Cys Gln Cys Leu Gln
 1               5                   10

( 2 ) INFORMATION FOR SEQ ID NO:14:

( i ) SEQUENCE CHARACTERISTICS:
        ( A ) LENGTH: 13 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:14:

Ala Ser Val Val Thr Glu Leu Arg Cys Gln Cys Leu Gln
 1               5                   10

( 2 ) INFORMATION FOR SEQ ID NO:15:

( i ) SEQUENCE CHARACTERISTICS:
        ( A ) LENGTH: 20 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:15:

Ala Val Leu Pro Arg Ser Ala Lys Glu Leu Arg Cys Gln Cys Ile Lys
 1               5                   10                  15

Thr Tyr Ser Lys
        20

( 2 ) INFORMATION FOR SEQ ID NO:16:

( i ) SEQUENCE CHARACTERISTICS:
        ( A ) LENGTH: 72 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:16:

Ser Ala Lys Glu Leu Arg Cys Gln Cys Ile Lys Thr Tyr Ser Lys Pro
 1               5                   10                  15

Phe His Pro Lys Phe Ile Lys Glu Leu Arg Val Ile Glu Ser Gly Pro
                    20                  25                  30

His Cys Ala Asn Thr Glu Ile Ile Val Lys Leu Ser Asp Gly Arg Glu
              35                  40                  45

Leu Cys Leu Asp Pro Lys Glu Asn Trp Val Gln Arg Val Val Glu Lys
         50                  55                  60

Phe Leu Lys Arg Ala Glu Asn Ser
65                  70

( 2 ) INFORMATION FOR SEQ ID NO:17:

( i ) SEQUENCE CHARACTERISTICS:
        ( A ) LENGTH: 70 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:17:

Ala Glu Leu Arg Cys Met Cys Ile Lys Thr Thr Ser Gly Ile His Pro
1                5                  10                  15

Lys Asn Ile Gln Ser Leu Glu Val Ile Gly Lys Gly Thr His Cys Asn
              20                  25                  30

Gln Val Glu Val Ile Ala Thr Leu Lys Asp Gly Arg Lys Ile Cys Leu
              35                  40                  45

Asp Pro Asp Ala Pro Arg Ile Lys Lys Ile Val Gln Lys Lys Leu Ala
         50                  55                  60

Gly Asp Glu Ser Ala Asp
65                  70

( 2 ) INFORMATION FOR SEQ ID NO:18:

( i ) SEQUENCE CHARACTERISTICS:
        ( A ) LENGTH: 73 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:18:

Ala Ser Val Ala Thr Glu Leu Arg Cys Gln Cys Leu Gln Thr Leu Gln
1                5                  10                  15

Gly Ile His Pro Lys Asn Ile Gln Ser Val Asn Val Lys Ser Pro Gly
              20                  25                  30

Pro His Cys Ala Gln Thr Glu Val Ile Ala Thr Leu Lys Asn Gly Arg
              35                  40                  45

Lys Ala Cys Leu Asn Pro Ala Ser Pro Ile Val Lys Lys Ile Ile Glu
         50                  55                  60

Lys Met Leu Asn Ser Asp Lys Ser Asn
65                  70

( 2 ) INFORMATION FOR SEQ ID NO:19:

( i ) SEQUENCE CHARACTERISTICS:
        ( A ) LENGTH: 73 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:19:

Ala Pro Leu Ala Thr Glu Leu Arg Cys Gln Cys Leu Gln Thr Leu Gln
1                5                  10                  15

Gly Ile His Leu Lys Asn Ile Gln Ser Val Lys Val Lys Ser Pro Gly
              20                  25                  30

```
Pro His Cys Ala Gln Thr Glu Val Ile Ala Thr Leu Lys Asn Gly Gln
        35                  40                  45

Lys Ala Cys Leu Asn Pro Ala Ser Pro Met Val Lys Lys Ile Ile Glu
        50                  55                  60

Lys Met Leu Lys Asn Gly Lys Ser Asn
65                  70
```

( 2 ) INFORMATION FOR SEQ ID NO:20:

( i ) SEQUENCE CHARACTERISTICS:
        ( A ) LENGTH: 73 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:20:

```
Ala Ser Val Val Thr Glu Leu Arg Cys Gln Cys Leu Gln Thr Leu Gln
1               5                   10                  15

Gly Ile His Leu Lys Asn Ile Gln Ser Val Asn Val Arg Ser Pro Gly
            20                  25                  30

Pro His Cys Ala Gln Thr Glu Val Ile Ala Thr Leu Lys Asn Gly Lys
        35                  40                  45

Lys Ala Cys Leu Asn Pro Ala Ser Pro Met Val Gln Lys Ile Ile Glu
        50                  55                  60

Lys Ile Leu Asn Lys Gly Ser Thr Asn
65                  70
```

( 2 ) INFORMATION FOR SEQ ID NO:21:

( i ) SEQUENCE CHARACTERISTICS:
        ( A ) LENGTH: 70 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:21:

```
Glu Ala Glu Glu Asp Gly Asp Leu Gln Cys Leu Cys Val Lys Thr Thr
1               5                   10                  15

Ser Gln Val Arg Pro Arg His Ile Thr Ser Leu Glu Val Ile Lys Ala
            20                  25                  30

Gly Pro His Cys Pro Thr Ala Gln Leu Ile Ala Thr Leu Lys Asn Gly
        35                  40                  45

Arg Lys Ile Cys Leu Asp Leu Gln Ala Pro Leu Tyr Lys Lys Ile Ile
        50                  55                  60

Lys Lys Leu Leu Glu Ser
65                  70
```

( 2 ) INFORMATION FOR SEQ ID NO:22:

( i ) SEQUENCE CHARACTERISTICS:
        ( A ) LENGTH: 76 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:22:

```
Val Pro Leu Ser Arg Thr Val Arg Cys Thr Cys Ile Ser Ile Asn Gln
1               5                   10                  15

Pro Val Asn Pro Arg Ser Leu Glu Lys Leu Glu Ile Ile Pro Ala Ser
            20                  25                  30

Gln Phe Cys Pro Arg Val Glu Ile Ile Ala Thr Met Lys Lys Lys Gly
```

```
                    35                     40                          45
Glu Lys Arg Cys Leu Asn Pro Glu Ser Lys Ala Ile Lys Asn Leu Leu
         50                     55                    60

Lys Ala Val Ser Lys Glu Met Ser Lys Arg Ser Pro
 65               70                   75
```

\* \* \* \* \*